United States Patent [19]

Spencer

[11] Patent Number: 4,907,600
[45] Date of Patent: Mar. 13, 1990

[54] BLOOD COLLECTOR CYLINDER WITH NEEDLE EJECTOR

[76] Inventor: Treesa A. Spencer, 21882 Winnebago, El Toro, Calif. 92630

[21] Appl. No.: 222,151

[22] Filed: Jul. 21, 1988

Related U.S. Application Data

[63] Continuation-in-part of Ser. No. 43,884, Apr. 29, 1987, abandoned.

[51] Int. Cl.$^4$ ............................................. A61B 5/14
[52] U.S. Cl. ............................. 128/764; 604/201; 604/240
[58] Field of Search ............... 128/760, 762–766, 128/771; 604/235, 240, 201, 223, 239, 241–243

[56] References Cited

U.S. PATENT DOCUMENTS

| | | | |
|---|---|---|---|
| 2,376,436 | 5/1945 | Lawshe | 604/240 X |
| 2,392,196 | 1/1946 | Smith | 604/235 X |
| 3,706,306 | 12/1972 | Berger et al. | 128/762 |
| 4,123,091 | 10/1978 | Cosentino | 604/240 X |
| 4,641,663 | 2/1987 | Juhn | 128/765 |
| 4,653,511 | 3/1987 | Goch | 128/763 |
| 4,710,170 | 12/1987 | Haber et al. | 604/110 |
| 4,731,059 | 3/1988 | Wanderer et al. | 128/764 X |
| 4,784,650 | 11/1988 | Coburn | 128/764 X |

FOREIGN PATENT DOCUMENTS

| | | | |
|---|---|---|---|
| 2451398 | 5/1976 | Fed. Rep. of Germany | 128/765 |
| 2815377 | 11/1978 | Fed. Rep. of Germany | 128/764 |
| 0334207 | 12/1903 | France | 604/231 |

*Primary Examiner*—Angela D. Sykes
*Attorney, Agent, or Firm*—Klein & Szekeres

[57] ABSTRACT

A blood collector system utilizes a standard disposable needle assembly and standard blood collecting and receiving tubes of the type sealed by a pierceable septum. The system has a hollow cylinder, including an internally apertured sleeve into which the needle assembly is mounted and into which the sealed blood collecting tubes are inserted to be pierced by a needle of the needle assembly. A member, such as a plate, is pivotably mounted to the cylinder. A hole in the plate accommodates the needle assembly while the needle assembly is retained in the cylinder. When the blood specimen collection is complete, the plate is moved in a pivoting motion whereby it catches the needle assembly and ejects it from the cylinder. The apparatus of the invention eliminates the need for a protective sheath to be replaced on the needle assembly before the needle assembly is discarded, and thereby minimizes the health care worker's exposure to accidental needle pricks.

8 Claims, 4 Drawing Sheets

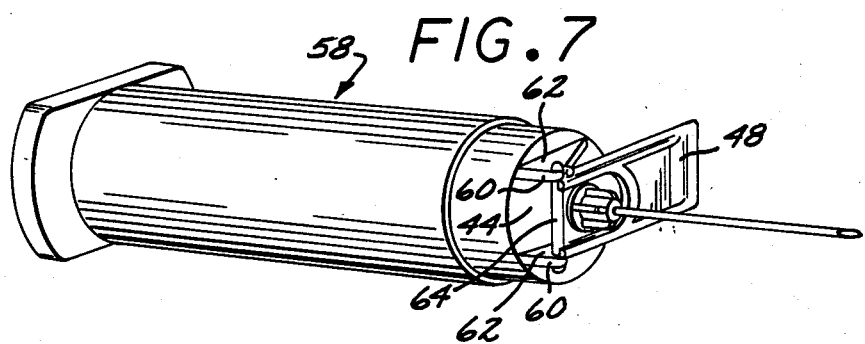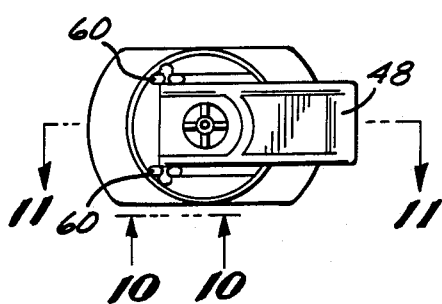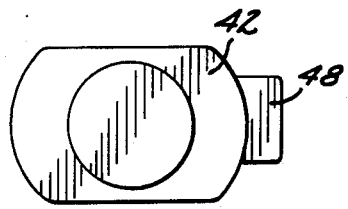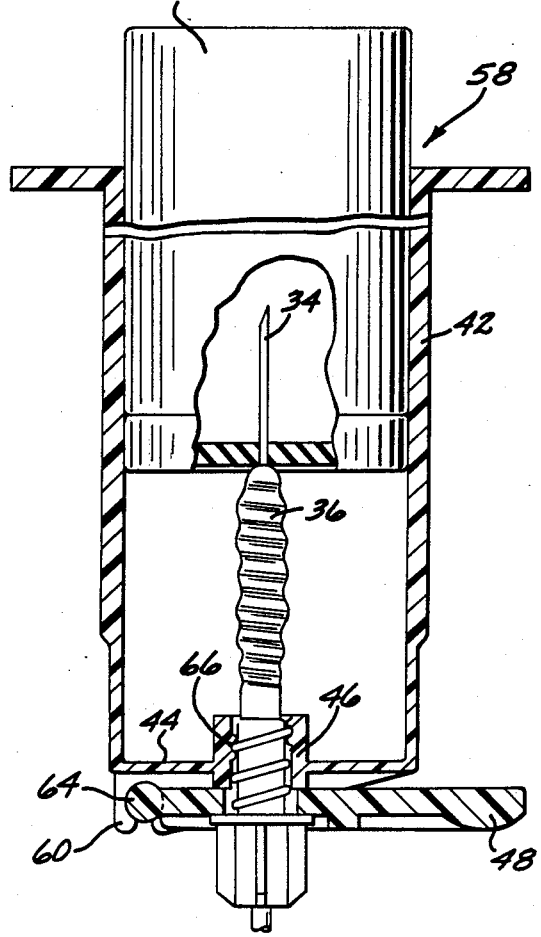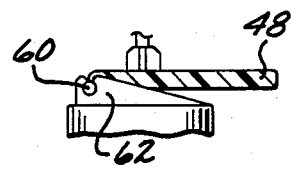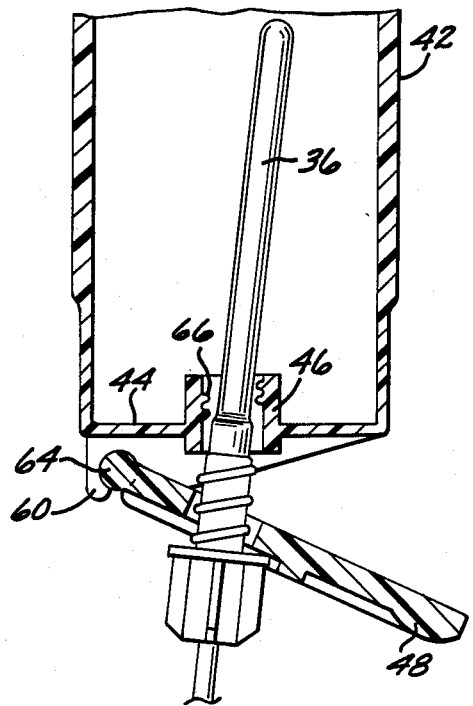

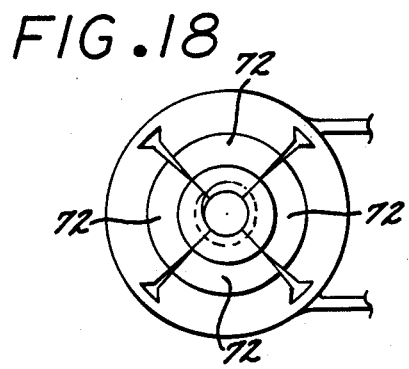
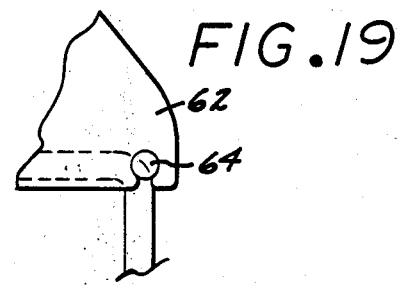
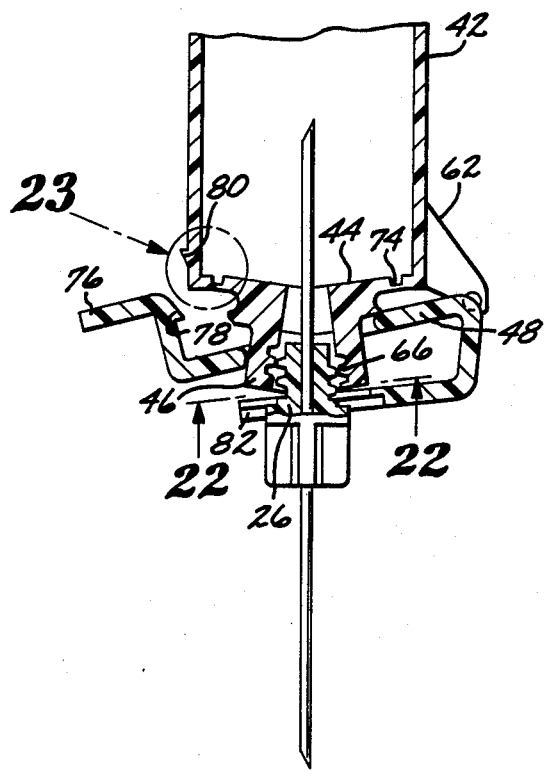
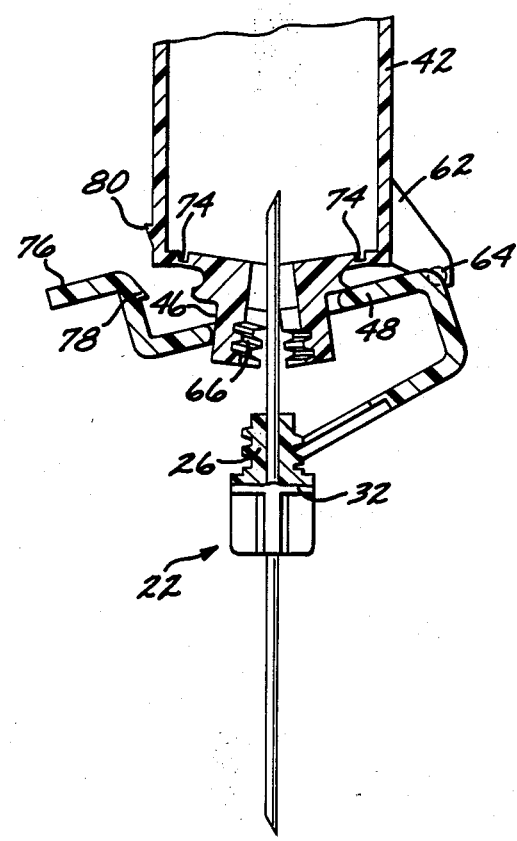
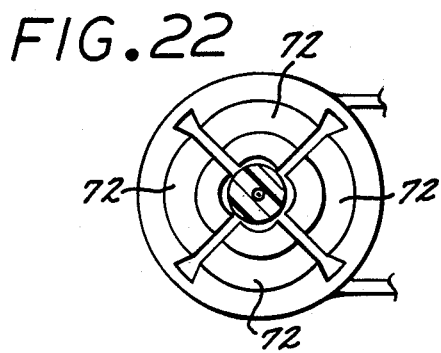
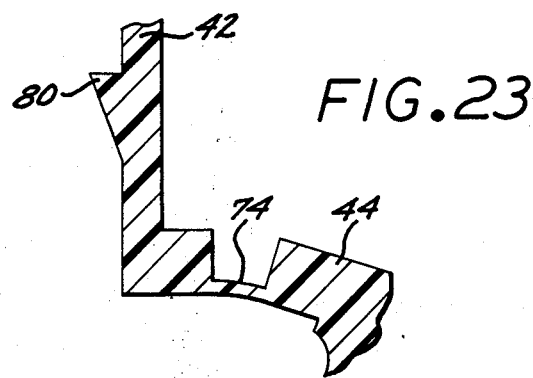

BLOOD COLLECTOR CYLINDER WITH NEEDLE EJECTOR

CROSS-REFERENCE TO RELATED APPLICATION

The present application is a continuation-in-part of my co-pending application Ser. No. 043,884 filed on Apr. 29, 1987, now abandoned.

BACKGROUND OF THE INVENTION

1. Field of the Invention

The present invention is directed to an improved blood specimen collection system for collecting blood from humans and domestic animals. More particularly, the present invention is directed to a blood specimen collector cylinder which includes an ejector for the needle used during the collection, whereby the used needle can be ejected and discarded without being touched by human hands.

2. Brief Description of the Prior Art

Blood specimen collectors have been known in the art for a long time. More particularly, hypodermic syringes and needles have been used in the art for a long time to draw blood samples from humans and domestic animals.

Current hospital and clinical practice, however, requires the taking of blood specimens to occur rapidly and with inexpensive and readily disposable equipment. Ordinary hypodermic syringe and needle combinations do not meet these requirements well. The below-described state-of-the-art blood collecting system, on the other hand, permits rapid collection of blood specimen and uses a disposable needle and a collection tube in which the collected blood specimen is initially received and in which it may be stored until desired blood tests are performed.

More particularly, and still with reference to the state-of-the-art blood collecting system, for the drawing of blood specimen, a standard disposable needle assembly is placed into a threaded hole in the end wall of a hollow cylinder. The standard disposable needle assembly includes an externally extending hollow needle which is used to "stick" the patient to draw blood, and another needle extending inwardly into the interior of the hollow cylinder. The two needles are coaxial and are in fluid communication with one another. The collection tube is sealed at one end with a pierceable rubber or like septum. The collection tube is placed within the interior of the cylinder so that the septum is pierced by the inwardly extending needle. The patient's blood is then drawn into the collection tube through the needles without coming into contact with the hollow cylinder.

After the collection tube is withdrawn from the cylinder, the needle assembly is discarded. For safety reasons this requires placement of a protective cap or sheath on the externally extending needle, and subsequent twisting of the needle assembly to free it from the threaded hole. Because during its normal, intended usage the hollow cylinder does not come into contact with the patient's blood, therefore normally it is not discarded each time after a blood specimen has been collected.

Although the above-summarized prior art blood specimen collecting apparatus works well, it has a serious disadvantage in that it is necessary to manipulate and touch the needle assembly after the needle has been in contact with the patient's blood. Such manipulation unfortunately gives rise to the possibility of accidental wounding or pricking of a health care worker by the needle which has been used to collect blood capable of transmitting infectious diseases. It is well known in the art that certain serious, even fatal, diseases, such as hepatitis and AIDS, may be spread in this manner, that is, through accidental contact with infected blood.

In light of the foregoing, there is a definite need in the art for a blood sample collecting system or apparatus in which exposure to contaminated needles is minimized or eliminated. This need has not been met in the prior art, although various devices have been made in the hypodermic syringe and related arts for drawing blood specimens and for performing and facilitating the process of injection of drugs with hypodermic syringes.

U.S. Pat. No. 3,706,306 describes a blood specimen collecting apparatus substantially of the type which is referred to in the foregoing brief description as "state-of-the-art". U.S. Pat. No. 2,393,196 describes a hypodermic syringe apparatus having a pivotable end piece to which a needle can be mounted. U.S. Pat. Nos. 4,653,511; 4,710,170; 4,123,091; 2,376,436; 4,641,663; French Pat. No. 334,207; German Offenlegungsschrift No. 2451398 and German Offelegungsschrift No. 2815377 describe still further blood specimen collector and syringe type devices which comprise the background of the present invention.

SUMMARY OF THE INVENTION

It is an object of the present invention to provide a blood specimen collecting system in which a used needle assembly can be discarded without being touched by human hands, thereby minimizing the health care worker's exposure to contaminated needles which may potentially spread dangerous or fatal diseases.

It is another object of the present invention to provide a blood specimen collecting system which meets the above-noted objective and which utilizes standard needle assemblies and blood sample collection tubes.

The foregoing and other objects and advantages are attained by a blood collecting system which utilizes standard blood collecting tubes having one of their ends sealed by a pierceable septum. A standard disposable needle assembly used in conjunction with the system includes coaxial first and second hollow needles in fluid communication with one another and an intermediate portion of enlarged diameter which is dimensioned to fit within an aperture provided in an end wall of a hollow cylinder. When the needle assembly is mounted into the cylinder, the first needle is axially extended and available to prick a patient to draw blood. The second needle is extended inwardly to pierce the septum of the standard blood collecting tube which is placed within the interior of the cylinder.

A member is mounted to the cylinder to engage the needle assembly and when desired to dislodge the needle assembly from its position in the aperture in the end wall of the cylinder. This obviates the need for the health care worker to touch the used needle assembly, or even to replace a protective sheath on the used needle before the used needle assembly with the sheath thereon is grasped (as in the prior art) and removed from the cylinder to be discarded.

In certain of the herein-described preferred embodiments the dislodging member is a plate pivotably mounted to the cylinder and having a hole which accommodates the needle assembly, and which catches and dislodges the needle assembly from its position within the cylinder when the member is pivoted with its free end away from the cylinder.

In other preferred embodiments of the present invention, the wall of a forwardly protruding sleeve provided in the end wall of the hollow cylinder is split into a plurality of pieces or segments. A plate pivotably mounted to the cylinder contains an opening. In the closed position of the plate relative to the cylinder, the opening engages and compresses the split pieces of the sleeve so as to firmly retain the intermediate portion of the standard disposable needle assembly. At the same time, in the closed position of the pivotable plate a portion of the plate engages a shoulder of the needle assembly. Blood specimen collection is performed in the just-described position of the pivotable plate. Thereafter, when it is desired to eject the needle assembly, the pivotable plate is simply pivoted by a health care worker whereby the split pieces or segments of the sleeve which hold the needle assembly are released by the opening in the pivotable plate. Consequently, the needle assembly is no longer retained by the aperture, and is expelled therefrom by the portion of the plate which is engaged below the shoulder. In certain preferred embodiments, the pivotably mounted plate is mounted to the cylinder with a living hinge.

The features of the present invention can be best understood, together with further objects and advantages, by reference to the following description, taken in connection with the accompanying drawings.

BRIEF DESCRIPTION OF THE DRAWINGS

FIG. 7 is a perspective view of a second preferred embodiment of the blood specimen collecting system or apparatus of the present invention;

FIG. 8 is a front view of the second preferred embodiment;

FIG. 9 is a rear view of the second preferred embodiment;

FIG. 10 is a cross-sectional view, the cross-section being taken on lines 10,10 of FIG. 9;

FIG. 11 is another cross-sectional view taken on lines 11,11 of FIG. 8, and

FIG. 12 is still another cross-sectional view, analogous to the cross-sectional view taken on lines 11,11 of FIG. 8, but showing a needle assembly in the stage of being removed from a hollow cylinder of the blood specimen collecting system of the present invention.

FIG. 18 is a front view of the third preferred embodiment with a pivotable plate folded away from the cylinder of the third preferred embodiment;

FIG. 19 is an enlarged view showing the mounting of the pivotable plate to the cylinder of the third preferred embodiment;

FIG. 20 is a partial cross-sectional view of the third preferred embodiment, showing the process of placing a standard disposable needle assembly into the blood collecting system of the third preferred embodiment;

FIG. 21 is a cross-sectional view of the third preferred embodiment, showing the process of ejecting a standard disposable needle assembly from the blood collecting system of the third preferred embodiment;

FIG. 22 is a view taken on lines 22, 22 of FIG. 20 and

FIG. 23 is an enlarged view of the area indicated by the Numeral 23 on FIG. 20.

DESCRIPTION OF THE PREFERRED EMBODIMENTS

Figure 1:
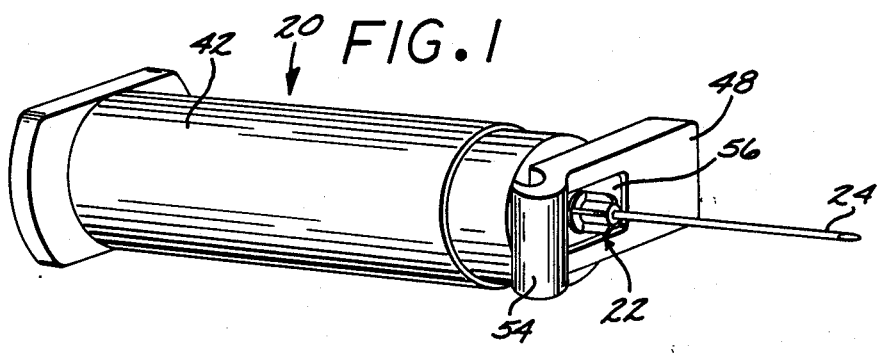
FIG. 1 is a perspective view of a first preferred embodiment of the blood specimen collecting system or apparatus of the present invention.
Figure 2:
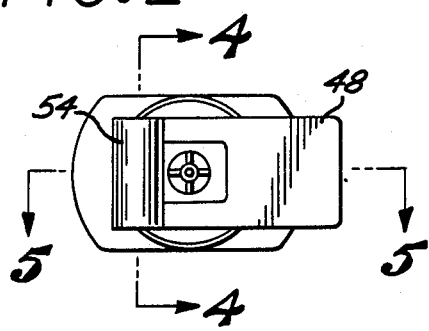
FIG. 2 is a front view of the first preferred embodiment.
Figure 3:
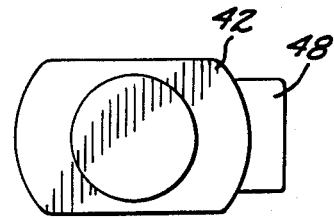
FIG. 3 is a rear view of the first preferred embodiment.
Figure 4:
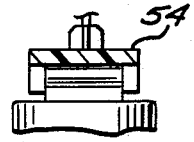
FIG. 4 is a cross-sectional view, the cross-section being taken on lines 4,4 of FIG. 3.
Figure 5:
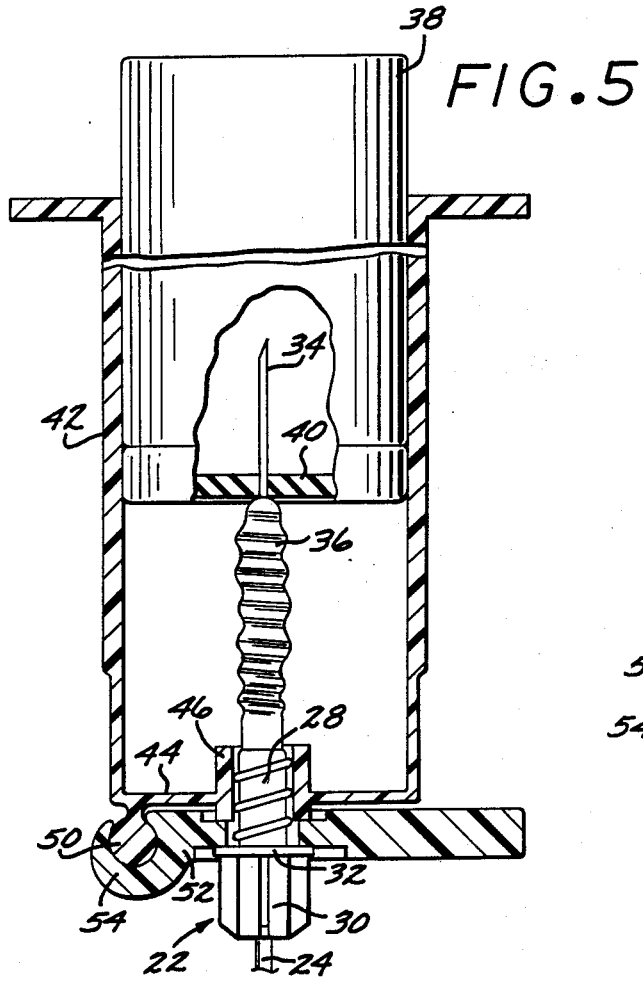
FIG. 5 is another cross-sectional view taken on lines 5,5 of FIG. 2.

The following specification taken in conjunction with the drawings set forth the preferred embodiments of the present invention. The embodiments of the invention disclosed herein are the best modes contemplated by the inventor for carrying out her invention in a commercial environment, although it should be understood that various modifications can be accomplished within the parameters of the present invention.

Referring now to FIGS. 1 through 6 of the appended drawings, a first preferred embodiment 20 of the blood specimen collector of the present invention is disclosed. It should be noted at the outset that the blood specimen collector of the present invention is designed and adapted to utilize standard disposable needle assemblies and standard blood collection tubes, both of which are ordinarily used in the art for the collection of blood specimens. Although these standard items do not, in and of themselves, comprise the present invention, they are described here first, to the extent necessary to explain and illuminate the present invention.

Thus, a standard needle assembly 22 includes a first needle 24 which is normally used to penetrate a patient's veins (or other parts of the patient's body) to draw blood. An intermediate portion of the needle assembly 22 is a plastic body 26 of larger diameter than the first needle 24. The plastic body 26 is substantially cylindrical, and has a threaded part 28 and a ribbed part 30, with the two being separated from each other by a radially extending shoulder 32. A second needle 34 extends from the plastic body 26 in a direction which is opposite to that of the first needle 24. The two needles 24 and 34 are hollow and in fluid communication with one another. In fact, for practical construction of the needle assembly 22, the two needles 24 and 34 comprise the same piece of metal to which the plastic body 26 is attached.

Still in accordance with standard practice in the art, the needle assembly 22 is usually packaged and stored in protective sheaths (not shown) which are separately removable from the first and second needles 24 and 34, respectively. Moreover, the second needle 34 usually carries a protective rubber or like sleeve 36 which may be retracted on the second needle 34, as is shown on FIG. 5.

The blood collection tubes 38 used in the present invention comprise tubular receptacles of glass or plastic, which have a resilient septum seal 40 penetrable by the second needle 34. The interior of the blood collection tube 38 is usually evacuated so as to contain partial vacuum. As it will be readily understood by those skilled in the art, the vacuum in the blood collection tube 38 eliminates the need for an air vent or vented needle during the blood collection process.

The appended drawing figures show a tubular, hollow cylinder 42 having a front wall 44 which includes a relatively short sleeve 46. Prior to taking of blood specimens the threaded portion 28 of the plastic body 26 is fitted into the sleeve 46, whereby the needle assembly 22 is mounted to the hollow cylinder 42. The blood collection tube 38 is placed and pushed into the cylinder 42 so that the second needle 34 penetrates the septum seal 40, as is specifically shown on FIG. 5. As it will be readily understood by those skilled in the art, under the above-described circumstances blood can be drawn from a patient's body into the blood collection tube 38.

After the first needle 24 is withdrawn from the patient's body, and the blood collection tube 38 is removed from the cylinder 42, the collected blood specimen can be stored in the collection tube 38. The needle assembly 22 which has come into contact with the patient's blood, must be discarded. The hereinafter-described novel features of the present invention facilitate the step of discarding the used needle assembly 22, and render it much less likely that a doctor, nurse, or other health care worker accidentally should prick or injure himself or herself with the used needle.

Thus, in accordance with the present invention, and referring still primarily to FIGS. 1 through 6, a plate 48 is pivotally mounted to the front wall 44 of the cylinder 42. In the herein-described first preferred embodiment 20, the front wall 44 includes a pivot pin 50. An edge 52 of the plate 48 includes a somewhat resilient plastic female pin receiver 54 which is fitted on the pin 50. The pin 50 and the pin receiver 54 jointly form a hinge which permits pivoting motion of the plate 48 relative to the front wall 44 of the cylinder 42.

The plate 48 includes an opening or hole 56 through which the needle assembly 22 is fitted when the needle assembly 22 is mounted into the cylinder 42. As is shown on FIG. 5, in the mounted position of the needle assembly 22, the plate 48 lies flat or substantially flat against the front wall 44 of the cylinder 32, and the plate 48 abuts the shoulder 32 of the needle assembly 22.

Figure 6:
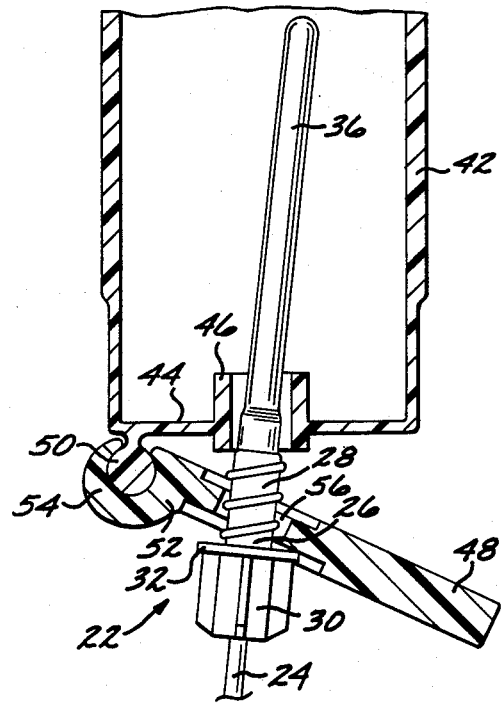
FIG. 6 is still another cross-sectional view, analogous to the cross-sectional view taken on lines 5,5 of FIG. 2, but showing a needle assembly in the stage of being removed from a hollow cylinder of the blood specimen collecting system of the present invention.
Figure 13:
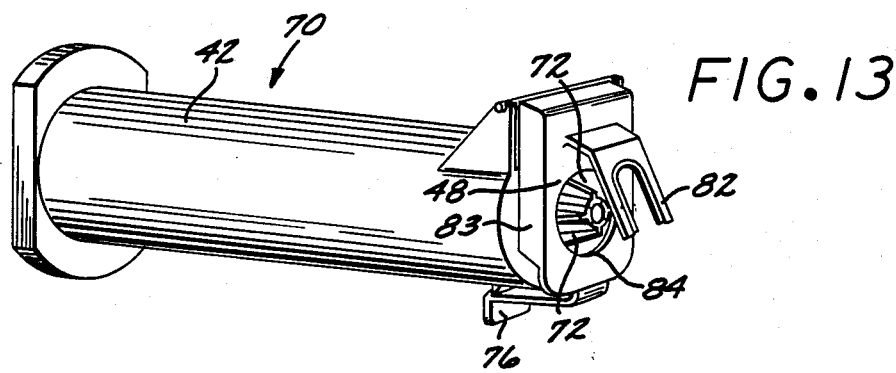
FIG. 13 is a perspective view of the third preferred embodiment.
Figure 14:
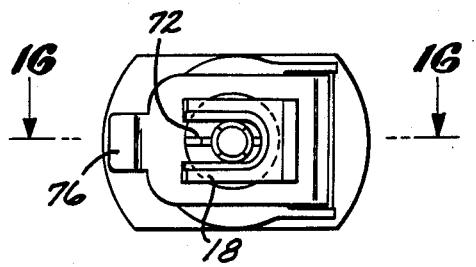
FIG. 14 is a front view of the third preferred embodiment.
Figure 15:
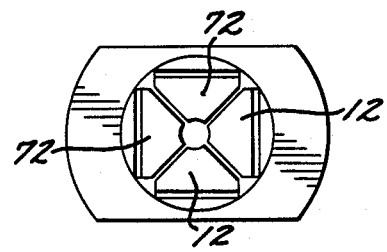
FIG. 15 is a rear view of the third preferred embodiment.
Figure 16:
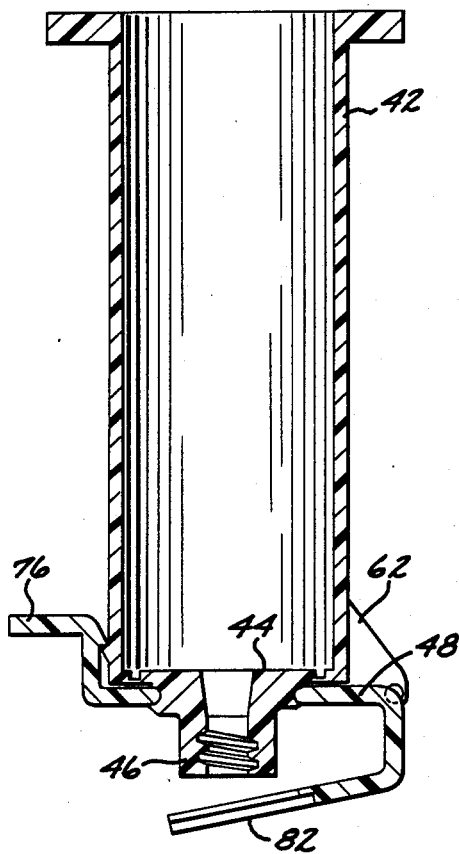
FIG. 16 is a cross-sectional view, the cross-section being taken on lines 16, 16 of FIG. 15.
Figure 17:
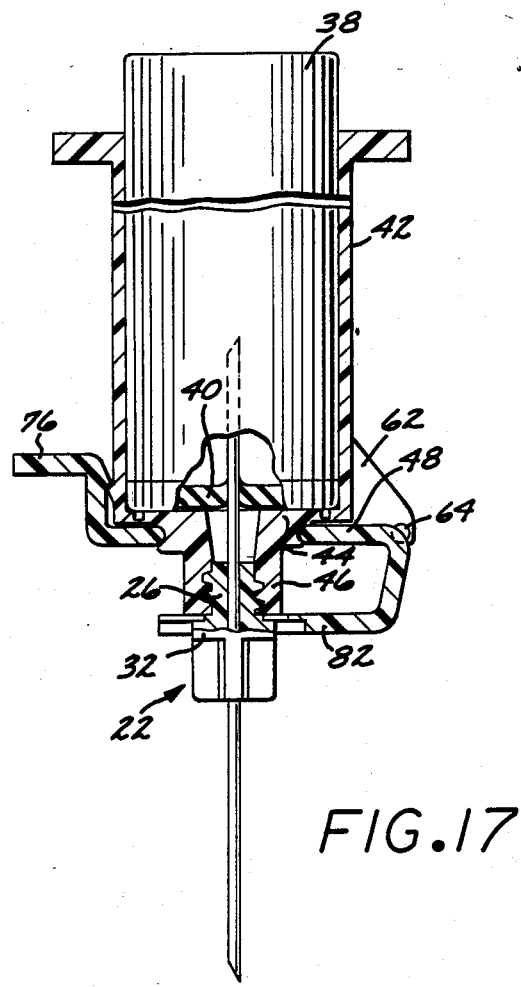
FIG. 17 is another cross-sectional view of the third preferred embodiment, analogous to the cross-sectional view taken on lines 16, 16 of FIG. 14, but showing a needle assembly and a blood collection tube mounted into the blood collecting system of the invention.

FIG. 6 shows how the pivotally mounted plate 48 is used to dislodge and eject the used needle assembly 22 from the cylinder 42. Thus, one edge of the plate 48 is grasped and moved by the health care worker (not shown) whereby the plate 48 pushes against the shoulder 32 and removes the needle assembly 22 from the sleeve 46. The needle assembly 22 is then allowed to fall out into a waste container (not shown), preferably into a type of waste container which is specifically designed for receipt and disposal of used hypodermic needles and the like.

It is still noted in connection with the first preferred embodiment 20 of the present invention, that the interior bore of the sleeve 46 is not threaded, even though ordinarily used "standard" needle assemblies include the threaded intermediate plastic portion 28.

It should be apparent from the foregoing that to dislodge or eject the needle assembly 22 from the cylinder 42, the health care worker's hands do not need to touch the needle assembly 22. For this reason, it is not necessary to replace the protective sheath (not shown) on the first needle 24 before the needle assembly 22 is ejected from the cylinder 42 and is discarded. It will be immediately appreciated by those skilled in the art that obviating the need to replace the sheath (not shown) on the first needle 24 before the needle assembly 22 is manipulated and discarded, is highly advantageous, because most accidental skin punctures with the used needle occur when the health care worker (not shown) attempts to fit a sheath (not shown) on the used needle.

Referring now to FIGS. 7 through 12 of the appended drawings, a second preferred embodiment 58 of the present invention is disclosed. The second preferred embodiment 58 is similar in many respects to the first preferred embodiment 20, and is therefore described here only to the extent necessary to describe the differences between the two preferred embodiments.

Thus, the hollow cylinder 42 of the second preferred embodiment 58 includes a pair of pin receivers 60 mounted to spaced ribs 62 disposed on the front wall 44 of the cylinder 42. The edge 52 of the pivotally mounted plate 48 has a pivot pin 64 which is mounted into the pin receivers 60 to form a hinge.

The aperture provided in the sleeve 46 of the front wall 44 of the cylinder 42 has a short female thread 66 which is complementary to threads of the plastic body 26. The thread 66 is approximately one turn or less. To permit ready demounting of the needle assembly 22 from the cylinder 42 by the pivoting motion of the plate 48, the female thread 66 in the sleeve 46 must be short, and cannot hold the needle assembly 22 too firmly.

Operation of the second preferred embodiment 58 is substantially the same as of the first preferred embodiment 20. The second preferred embodiment 58 also offers the same advantage over the prior art, that is, it minimizes exposure of health care workers to accidental needle pricks by used needles during blood specimen collecting procedures.

Referring now to FIGS. 13 through 23 of the appended drawings, a third preferred embodiment 70 of the blood specimen collector of the present invention is disclosed. Like the previously described embodiments, the third preferred embodiment 70 is also used in conjunction with the standard disposable needle assembly 22 and with the standard blood collection tube 38 having the septum seal 40. Principal differences between the previously described embodiments and the third preferred embodiment 70 is in the construction of the portions of third embodiment 70 which retain the needle assembly 22 while a blood specimen is collected, and which eject the used needle assembly 22 after the collection is completed.

Referring still to FIGS. 13-23, the third preferred embodiment 70 includes the tubular hollow cylinder 42. The front wall 44 of the hollow cylinder 42 includes a sleeve 46. The sleeve 46 of the third preferred embodiment 70 is, however, more forwardly disposed than the sleeves of the previously described embodiments, and comprises split segments or pieces 72, as is shown on FIGS. 13, 15, 18, and 22. The interior of the sleeve 46 has female threads 66 which are complementary to the threads of the intermediate plastic body 26 of the needle assembly 22. The entire front wall 44 of the cylinder 42 of the third preferred embodiment 70 is mounted through a narrow hinge-like piece to the rest of the plastic body of the cylinder 42. The hinge-like piece 74 is perhaps best shown on FIGS. 20, 21 and 23. It should already be apparent from the foregoing description, that unless the segments 72 of the sleeve 46 are held together by an additional member, the sleeve 46 of the third preferred embodiment 70 is incapable of retaining the needle assembly 22, or is able to retain the needle assembly 22 only very weakly.

With reference to the foregoing, retention of the needle assembly 22 is provided in the third preferred embodiment 70 by a retainer plate 48. The retainer plate 48, similarly to the retainer plate of the second preferred embodiment 58, is mounted through its pivot pin 64 into a pair of pin receivers 60 which are themselves mounted to spaced ribs 62 attached to the cylinder 42.

The retainer plate 48 of the third preferred embodiment 70 includes an L-shaped extension 76 which is designed to be manipulated by the thumb (not shown) of a health care worker (not shown). The L-shaped extension 76 also has a protrusion 78 which is capable of engaging a second protrusion 80 on the cylinder 42, 50 as to reversibly lock the retainer plate 48 into a closed position relative to the cylinder 42. The retainer plate 48 still further includes a forwardly extending forked plate 82, the purpose of which is to eject the needle assembly 22. This is described in more detail below. Two parallel disposed side plates 83 of the retainer plate 48, shown on FIG. 13, touch the front wall 44 of the cylinder 42 in the closed position of the retainer plate 48.

The retainer plate 48 also has an opening 84 of such dimensions that in the locked position of the plate 48 the interior wall of the opening 84 engages the exterior of the segments 72 of the sleeve 46, so as to form a substantially firm threaded opening in the sleeve 46. The threaded opening in the sleeve 46, when engaged or held by the locked retainer plate 48, is capable of firmly retaining the needle assembly 22 through its threaded plastic body 26. This is well shown on FIG. 17; the Figure shows the retainer plate 48 in a locked position relative to the cylinder 42.

Referring now primarily to FIG. 20, the process is illustrated wherein the needle assembly 22 is placed into the third preferred embodiment 70. During this process, the retainer plate 48 is not locked, but is disposed in such position that the needle assembly 22 can be placed through the opening 84. After the needle assembly 22 has been inserted into the sleeve 46, the retainer plate 48 is locked, as is shown on FIG. 17, whereby the needle assembly 22 is firmly engaged. In the locked position of the retainer plate 48 the forked plate 82 is disposed below the radially extending shoulder 32 of the plastic body 26, and is slightly compressed, so that it is resiliently biased by the shoulder 32.

Ejection of the needle assembly 22 from the third preferred embodiment 70, without exposure of human hands (not shown) to the proximity of contaminated and potentially highly infectious used needle, is shown on FIG. 21. In order to eject the needle assembly 22 a health care worker (not shown) simply unlocks the L-shaped extension of the retainer plate 48. The slightly compressed but resilient plastic material of the forked plate extension 82 then ejects the needle assembly 22 from the sleeve 46, the segments 72 of which are no longer held together by the opening 84 in the retainer plate 48.

A fourth preferred embodiment of the present invention is constructed substantially similar to the third preferred embodiment 70, except that the retainer plate 48 is not a separately formed plastic piece, but rather it is molded or otherwise fabricated together with the plastic cylinder 42, and is attached thereto by a living hinge. Such living hinges are well known in the plastic manufacturing arts.

The blood collecting system or apparatus of the present invention may be manufactured from such materials which are well known in the art. More particularly, the needle assembly 22 and the blood collection tubes 38 are state-of-the-art, and can be made from medical grade plastic, rubber, and stainless steel materials. The cylinder 42 and the needle assembly ejecting plate mounted to it is made from suitable plastic, such as polypropylene, polyethylene, polystyrene or polyvinyl chloride.

Several modifications of the above-described invention in terms of specific construction and materials may become readily apparent to those skilled in the art in light of the foregoing disclosure. Therefore, the scope of the present invention should be interpreted solely from the following claims as such claims are read in light of the disclosure.

What is claimed is:

1. A cylinder and needle assembly ejector used for collecting blood samples in conjunction with a blood sample collector tube and with a needle assembly, the collector tube adapted to fit at least partially within the hollow interior of the cylinder, the collector tube being sealed at one of its ends by a septum pierceable with a needle, and the needle assembly having an intermediate portion which is dimensioned to fit and be mounted in an apertured sleeve formed in an end wall of the hollow cylinder, a first hollow needle portion extending axially outwardly from the hollow cylinder, and a second hollow needle portion extending axially inwardly into the interior of the cylinder, the first and second hollow needle portions being in fluid communication with one another, the first hollow needle portion being adapted to pierce a person's veins, and the second hollow needle portion being adapted to pierce the septum, the cylinder and needle assembly ejector comprising:

manually actuable means mounted to the cylinder for ejecting the needle assembly from engagement with the hollow cylinder, the means for ejecting capable of operating without the needle assembly being touched by human hands, whereby after use, the needle assembly can be discarded while touching of the same by human hands is avoided, the sleeve of the cylinder comprising a plurality of split segments, and the manually actuable means further comprising means for engaging the split segments of the sleeve for forming a firm internal aperture wherein the needle assembly is mountable.

2. The cylinder and needle assembly ejector of claim 1 wherein the manually actuable means is a retainer plate pivotably mounted to the cylinder, the retainer plate having an internal opening dimensioned to engage the split segments of the sleeve when the retainer plate is in a closed position relative to the cylinder, and wherein the retainer plate further comprises a second plate fixedly but resiliently attached to the retainer plate, said retainer plate being compressedly biased by the needle assembly when the needle assembly is retained in the sleeve.

3. In an apparatus for collecting blood specimens from humans or domestic animals, the apparatus including, in combination, a hollow cylinder having an end wall and an apertured sleeve formed in the end wall adapted to receive a removably mounted needle assembly; a blood sample collector tube adapted to fit at least partially within the hollow interior of the cylinder, the collector tube being sealed at one of its ends by a septum pierceable with a needle; a needle assembly having an intermediate portion which is dimensioned to fit and be mounted in the apertured sleeve of the hollow cylinder, a first hollow needle portion extending axially outwardly from the hollow cylinder, and a second hollow needle portion extending axially inwardly into the interior of the cylinder, the first and second hollow needle portions being in fluid communication with one another, the first hollow needle portion being adapted to pierce a person's veins, and the second hollow needle portion being adapted to pierce the septum, the improvement comprising:

(1) means mounted to the cylinder for ejecting the needle assembly from its position mounted in the aperture, the means for ejecting being capable of demounting the needle assembly from the cylinder without need for human hands to touch the needle assembly; (2) the apertured sleeve comprising a plurality of split segments; (3) means for reversibly engaging the split segments for forming a firm sleeve from said split segments, and (4) wherein the means for ejecting includes a plate which is slightly compressed and biased by the needle assembly when the needle assembly is firmly mounted into the sleeve.

4. A blood specimen collecting system comprising in combination:

a hollow cylinder having an end wall wherein an aperture sleeve is formed from a plurality of split segments, the apertured sleeve comprising means for retaining a needle assembly when the split segments are firmly held together;

a blood sample collector tube adapted to fit at least partially within the hollow interior of the cylinder, the collector tube being sealed at one of its ends by a septum pierceable with a needle;

a needle assembly having an intermediate portion which is dimensioned to fit and to be mounted in the apertured sleeve of the hollow cylinder, a first hollow needle portion extending axially outwardly from the hollow cylinder, and a second hollow needle portion extending axially inwardly into the interior of the cylinder, the first and second hollow needle portions being in fluid communication with one another, the first hollow needle portion being adapted to pierce a person's veins, and the second hollow needle portion being adapted to pierce the septum;

first means mounted to the cylinder which is capable of occupying at least two positions relative to the cylinder, the first position being characterized by the first means holding the split segments of the apertured sleeve firmly together, whereby the needle assembly is firmly retained in the sleeve, the first means having a second position relative to the cylinder where the split segments of the sleeve are not held, and second means mounted to the cylinder for ejecting the needle assembly from its position mounted into the sleeve, the means for ejecting capable of demounting the needle assembly from the cylinder without need for human hands to touch the needle assembly.

5. The blood specimen collecting system of claim 4 wherein the first and second means comprise a plate pivotably mounted to the cylinder, the plate having an opening the walls of which engage and firmly hold the split segments of the sleeve in the first position of the plate relative to the cylinder, the plate carrying a resiliently mounted second plate which is compressed by the needle assembly when the needle assembly is firmly mounted into the sleeve in the first position of the plate, the second plate comprising the means for ejecting.

6. The blood specimen collecting system of claim 5 wherein the sleeve is internally threaded.

7. The blood specimen collecting system of claim 6 wherein the plate is pivotably mounted to the cylinder by a hinge pin.

8. The blood specimen collecting system of claim 6 wherein the plate is pivotably mounted to the cylinder by a living hinge.

* * * * *